(12) United States Patent
Gervais et al.

(10) Patent No.: US 8,414,919 B2
(45) Date of Patent: *Apr. 9, 2013

(54) SUSTAINED DRUG RELEASE COMPOSITION

(75) Inventors: Sonia Gervais, Laval (CA); Damon Smith, Saint-Laurent (CA); Pauline Contamin, Magny en Vexin (FR); Rachid Ouzerourou, Anjou (CA); My Linh Ma, Saint-Laurent (CA)

(73) Assignee: Angelini Labopharm, LLC, Princeton, NJ (US)

( * ) Notice: Subject to any disclaimer, the term of this patent is extended or adjusted under 35 U.S.C. 154(b) by 28 days.

This patent is subject to a terminal disclaimer.

(21) Appl. No.: 12/905,567

(22) Filed: Oct. 15, 2010

(65) Prior Publication Data

US 2011/0027370 A1    Feb. 3, 2011

Related U.S. Application Data

(63) Continuation of application No. 11/519,189, filed on Sep. 11, 2006.

(60) Provisional application No. 60/715,162, filed on Sep. 9, 2005.

(51) Int. Cl.
*A61K 9/20* (2006.01)
*A61K 9/14* (2006.01)

(52) U.S. Cl.
USPC ............................ 424/464; 424/465; 424/484

(58) Field of Classification Search .................. None
See application file for complete search history.

(56) References Cited

U.S. PATENT DOCUMENTS

| | | |
|---|---|---|
| 2,987,445 A | 6/1961 | Levesque |
| 3,087,860 A | 4/1963 | Endicott et al. |
| 3,336,200 A | 8/1967 | Krause et al. |
| 3,381,009 A | 4/1968 | Palazzo et al. |
| 3,652,589 A | 3/1972 | Flick et al. |
| 4,131,675 A | 12/1978 | Silvestrini |
| 4,353,887 A | 10/1982 | Hess et al. |
| 4,465,660 A * | 8/1984 | David et al. ............... 424/467 |
| 4,547,359 A * | 10/1985 | Zierenberg et al. ........... 424/468 |
| 4,595,587 A | 6/1986 | Zierenberg et al. |
| 4,683,131 A | 7/1987 | Zierenberg et al. |
| 4,820,522 A | 4/1989 | Radebaugh et al. |
| 4,824,677 A | 4/1989 | Shah et al. |
| 4,906,632 A | 3/1990 | Silvestrini et al. |
| 4,938,968 A | 7/1990 | Mehta |
| 4,968,509 A | 11/1990 | Radebaugh et al. |
| 5,004,613 A | 4/1991 | Radebaugh et al. |
| 5,126,145 A | 6/1992 | Evenstad et al. |
| 5,132,116 A | 7/1992 | Sournac et al. |
| 5,133,974 A | 7/1992 | Paradissis et al. |
| 5,273,760 A | 12/1993 | Oshlack et al. |
| 5,286,493 A | 2/1994 | Oshlack et al. |
| 5,336,691 A | 8/1994 | Raffa et al. |
| 5,407,686 A | 4/1995 | Patel et al. |
| 5,414,129 A | 5/1995 | Cherkez et al. |
| 5,427,799 A | 6/1995 | Valentine et al. |
| 5,451,409 A | 9/1995 | Rencher et al. |
| 5,456,921 A | 10/1995 | Mateescu et al. |
| 5,478,577 A | 12/1995 | Sackler et al. |
| 5,520,931 A | 5/1996 | Persson et al. |
| 5,560,331 A | 10/1996 | Komatsu et al. |
| 5,562,924 A | 10/1996 | Perrier et al. |
| 5,580,578 A | 12/1996 | Oshlack et al. |
| 5,591,452 A | 1/1997 | Miller et al. |
| 5,595,762 A | 1/1997 | Derrieu et al. |
| 5,601,842 A | 2/1997 | Bartholomaeus |
| 5,603,956 A | 2/1997 | Mateescu et al. |
| 5,616,343 A | 4/1997 | Cartilier et al. |
| 5,639,476 A | 6/1997 | Oshlack et al. |
| 5,663,279 A | 9/1997 | Kuiper et al. |
| 5,672,360 A | 9/1997 | Sackler et al. |
| 5,672,755 A | 9/1997 | Lerman et al. |
| 5,681,585 A | 10/1997 | Oshlack et al. |
| 5,773,031 A | 6/1998 | Shah et al. |
| 5,776,492 A | 7/1998 | Betzing et al. |

(Continued)

FOREIGN PATENT DOCUMENTS

| | | |
|---|---|---|
| CA | 970688 | 7/1975 |
| CA | 2280534 | 8/1998 |

(Continued)

OTHER PUBLICATIONS

Adler, L. et al., "A Comparison of Once-Daily Tramadol with Normal Release Tramadol in the Treatment of Pain in Osteoarthritis," The Journal of Rheumatology 2002, vol. 29, No. 10, pp. 2196-2199.

(Continued)

*Primary Examiner* — Susan Tran
(74) *Attorney, Agent, or Firm* — Goodwin Procter LLP

(57) ABSTRACT

The invention relates to a sustained release formulation for delivering one or more pharmaceutically active agents. The formulation comprises cross-linked high amylose starch and at least one pharmaceutically active agent, and optionally can be subdivided into smaller dosage forms where the smaller dosage forms have substantially the same sustained release properties as the formulation from which they were derived. The formulations can provide sustained release for up to at least 24 hours, and because of their divisability permits a recipient of the active agent or the person administering the active agent to titrate the dosage of the agent.

10 Claims, 4 Drawing Sheets

U.S. PATENT DOCUMENTS

| | | |
|---|---|---|
| 5,780,057 A | 7/1998 | Conte et al. |
| 5,807,575 A | 9/1998 | Dumoulin et al. |
| 5,814,338 A | 9/1998 | Veronesi et al. |
| 5,843,480 A | 12/1998 | Miller et al. |
| 5,849,240 A | 12/1998 | Miller et al. |
| 5,874,620 A | 2/1999 | Lerman et al. |
| 5,877,351 A | 3/1999 | Anderson |
| 5,879,705 A | 3/1999 | Heafield et al. |
| 5,879,707 A | 3/1999 | Cartilier et al. |
| 5,885,615 A | 3/1999 | Chouinard et al. |
| 5,888,545 A | 3/1999 | Landgraf et al. |
| 5,891,471 A | 4/1999 | Miller et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 5,981,592 A | 11/1999 | Wechter et al. |
| 6,077,537 A * | 6/2000 | Booth et al. .......... 424/468 |
| 6,103,261 A | 8/2000 | Chasin et al. |
| 6,120,803 A | 9/2000 | Wong et al. |
| 6,129,205 A | 10/2000 | Ergenbright et al. |
| 6,129,933 A | 10/2000 | Oshlack et al. |
| 6,143,322 A | 11/2000 | Sackler et al. |
| 6,143,325 A | 11/2000 | Dennis et al. |
| 6,143,328 A | 11/2000 | Heafield et al. |
| 6,143,353 A | 11/2000 | Oshlack et al. |
| 6,156,342 A | 12/2000 | Sriwongjanya et al. |
| 6,156,343 A | 12/2000 | Morita et al. |
| 6,162,467 A | 12/2000 | Miller et al. |
| 6,190,591 B1 | 2/2001 | van Lengerich |
| 6,210,714 B1 | 4/2001 | Oshlack et al. |
| 6,211,229 B1 | 4/2001 | Kavey |
| 6,214,331 B1 | 4/2001 | Vanderhoff et al. |
| 6,228,875 B1 | 5/2001 | Tsai et al. |
| 6,238,698 B1 | 5/2001 | Cremer et al. |
| 6,245,356 B1 | 6/2001 | Baichwal |
| 6,245,357 B1 | 6/2001 | Edgren et al. |
| 6,245,387 B1 | 6/2001 | Hayden |
| 6,248,363 B1 | 6/2001 | Patel et al. |
| 6,254,881 B1 | 7/2001 | McNally et al. |
| 6,254,887 B1 | 7/2001 | Miller et al. |
| 6,261,599 B1 | 7/2001 | Oshlack et al. |
| 6,277,887 B1 | 8/2001 | Young |
| 6,284,273 B1 | 9/2001 | Lenaerts et al. |
| 6,287,599 B1 | 9/2001 | Burnside et al. |
| 6,294,195 B1 | 9/2001 | Oshlack et al. |
| 6,306,438 B1 | 10/2001 | Oshlack et al. |
| 6,316,031 B1 | 11/2001 | Oshlack et al. |
| 6,326,027 B1 | 12/2001 | Miller et al. |
| 6,326,404 B1 | 12/2001 | Koegel et al. |
| 6,335,033 B2 | 1/2002 | Oshlack et al. |
| 6,339,105 B1 | 1/2002 | Kamin et al. |
| 6,372,255 B1 | 4/2002 | Saslawski et al. |
| 6,387,404 B2 | 5/2002 | Oshlack et al. |
| 6,399,096 B1 | 6/2002 | Miller et al. |
| 6,419,957 B1 | 7/2002 | Lenaerts et al. |
| 6,451,350 B1 | 9/2002 | Bartholomaeus et al. |
| 6,498,196 B1 | 12/2002 | Roberts et al. |
| 6,558,701 B2 | 5/2003 | Bartholomaeus et al. |
| 6,569,463 B2 | 5/2003 | Patel et al. |
| 6,572,885 B2 | 6/2003 | Oshlack et al. |
| 6,576,260 B2 | 6/2003 | Bartholomaeus et al. |
| 6,586,006 B2 | 7/2003 | Roser et al. |
| 6,593,373 B2 | 7/2003 | Koegel et al. |
| 6,607,748 B1 | 8/2003 | Lenaerts et al. |
| 6,632,640 B1 | 10/2003 | Lee et al. |
| 6,635,279 B2 | 10/2003 | Kolter et al. |
| 6,645,537 B2 | 11/2003 | Sweeney et al. |
| 6,659,373 B1 | 12/2003 | Heren et al. |
| 6,660,774 B2 | 12/2003 | Christoph et al. |
| 6,685,964 B1 | 2/2004 | Bartholomaeus et al. |
| 6,723,343 B2 | 4/2004 | Kugelmann et al. |
| 6,733,783 B2 | 5/2004 | Oshlack et al. |
| 6,743,442 B2 | 6/2004 | Oshlack et al. |
| 6,806,293 B1 | 10/2004 | Zamir et al. |
| 6,806,294 B2 | 10/2004 | Wimmer et al. |
| 6,863,901 B2 | 3/2005 | Hirsh et al. |
| 6,923,988 B2 | 8/2005 | Patel et al. |
| 6,962,717 B1 | 11/2005 | Huber et al. |
| 6,968,551 B2 | 11/2005 | Hediger et al. |
| 7,074,430 B2 | 7/2006 | Miller et al. |
| RE39,221 E | 8/2006 | Raffa et al. |
| 7,083,807 B2 | 8/2006 | Fanara et al. |
| 7,413,749 B2 | 8/2008 | Wright et al. |
| 7,829,120 B2 | 11/2010 | Gervais et al. |
| 7,988,998 B2 | 8/2011 | Lenaerts et al. |
| 2001/0019725 A1 | 9/2001 | Miller et al. |
| 2001/0036477 A1 | 11/2001 | Miller et al. |
| 2001/0038852 A1 | 11/2001 | Kolter et al. |
| 2002/0008133 A1 | 1/2002 | Imasaki et al. |
| 2002/0012701 A1 | 1/2002 | Kolter et al. |
| 2002/0032239 A1 | 3/2002 | Koegel et al. |
| 2002/0044966 A1 | 4/2002 | Bartholomaeus et al. |
| 2002/0052411 A1 | 5/2002 | Gobel et al. |
| 2002/0055544 A1 | 5/2002 | Kamin et al. |
| 2002/0106408 A1 | 8/2002 | Bacon et al. |
| 2002/0165246 A1 | 11/2002 | Holman |
| 2002/0176888 A1 | 11/2002 | Bartholomaeus et al. |
| 2003/0021846 A1 | 1/2003 | Kolter et al. |
| 2003/0035835 A1 | 2/2003 | Bartholomaeus et al. |
| 2003/0035837 A1 | 2/2003 | Sackler et al. |
| 2003/0044464 A1 | 3/2003 | Ziegler et al. |
| 2003/0054032 A1 | 3/2003 | Oshlack et al. |
| 2003/0068371 A1 | 4/2003 | Oshlack et al. |
| 2003/0068375 A1 | 4/2003 | Wright et al. |
| 2003/0069314 A1 | 4/2003 | Christoph et al. |
| 2003/0092724 A1 | 5/2003 | Kao et al. |
| 2003/0104061 A1 | 6/2003 | Bartholomaeus et al. |
| 2003/0143270 A1 | 7/2003 | Deboeck et al. |
| 2003/0148992 A1 | 8/2003 | Block et al. |
| 2003/0152627 A1 | 8/2003 | Beckert et al. |
| 2003/0158242 A1 | 8/2003 | Kugelmann |
| 2003/0180362 A1 | 9/2003 | Park et al. |
| 2004/0131671 A1 | 7/2004 | Zhang et al. |
| 2004/0136924 A1 | 7/2004 | Boyd et al. |
| 2004/0185096 A1 | 9/2004 | Oshlack et al. |
| 2004/0202716 A1 | 10/2004 | Chan et al. |
| 2004/0259956 A1 | 12/2004 | Wright et al. |
| 2005/0003002 A1 | 1/2005 | Ziegler et al. |
| 2005/0157382 A1 | 7/2005 | Kafka et al. |
| 2005/0256131 A1 | 11/2005 | Coester |
| 2005/0276852 A1 | 12/2005 | Davis et al. |
| 2006/0009465 A1 | 1/2006 | Edgar et al. |
| 2006/0111307 A1 | 5/2006 | Robbins |
| 2006/0115530 A1 | 6/2006 | Pettersson et al. |
| 2006/0172006 A1 | 8/2006 | Lenaerts et al. |
| 2006/0193911 A1 | 8/2006 | Ketsela et al. |
| 2006/0240107 A1 | 10/2006 | Lenaerts et al. |
| 2006/0269603 A1 | 11/2006 | Brown Miller et al. |
| 2007/0003618 A1 | 1/2007 | Lenaerts et al. |
| 2007/0048376 A1 | 3/2007 | Baichwal et al. |
| 2007/0128269 A1 | 6/2007 | Gervais et al. |
| 2007/0128275 A1 | 6/2007 | Gervais et al. |
| 2007/0237816 A1 | 10/2007 | Finkelstein |
| 2008/0096872 A1 | 4/2008 | Friedman |
| 2009/0047345 A9 | 2/2009 | Lenaerts et al. |
| 2009/0238870 A1 | 9/2009 | Fonknechten et al. |
| 2011/0015205 A1 | 1/2011 | Gervais et al. |
| 2011/0021535 A1 | 1/2011 | Gervais et al. |
| 2011/0033537 A1 | 2/2011 | Gervais et al. |

FOREIGN PATENT DOCUMENTS

| | | |
|---|---|---|
| CA | 2295469 | 7/2000 |
| CA | 2414349 | 1/2002 |
| CA | 2433668 | 6/2002 |
| CA | 2503155 | 5/2004 |
| CA | 2503361 | 5/2004 |
| CA | 2489855 | 4/2005 |
| CL | 172000 | 10/2000 |
| DE | 4315525 | 11/1994 |
| DE | 4329794 | 3/1995 |
| DE | 19530575 | 2/1997 |
| DE | 19901683 | 7/2000 |
| DE | 19901686 | 7/2000 |
| DE | 19901687 | 7/2000 |
| DE | 19940740.1 | 3/2001 |

| | | |
|---|---|---|
| DE | 19940944.7 | 3/2001 |
| DE | 10023699.5 | 4/2001 |
| DE | 19947747 | 4/2001 |
| EP | 0299877 | 1/1989 |
| EP | 0566709 | 10/1993 |
| EP | 0624366 | 11/1994 |
| EP | 0636370 | 2/1995 |
| EP | 0642788 | 3/1995 |
| EP | 0654263 | 5/1995 |
| EP | 0699436 | 3/1996 |
| EP | 0729751 | 9/1996 |
| EP | 0759296 | 2/1997 |
| EP | 0785775 | 7/1997 |
| EP | 0864325 | 9/1998 |
| EP | 1020183 | 7/2000 |
| EP | 1020185 | 7/2000 |
| EP | 1020186 | 7/2000 |
| EP | 1138320 | 10/2001 |
| EP | 1190712 | 3/2002 |
| EP | 1207866 | 5/2002 |
| EP | 1207867 | 5/2002 |
| EP | 1207868 | 5/2002 |
| EP | 1217998 | 7/2002 |
| EP | 1468679 | 10/2004 |
| EP | 1527775 | 5/2005 |
| EP | 1576986 | 9/2005 |
| EP | 1627633 | 2/2006 |
| GB | 2284760 | 6/1995 |
| JP | 7-19339 | 4/1995 |
| JP | 10-095801 | 4/1998 |
| NZ | 333401 | 10/1999 |
| WO | WO-94/02121 | 2/1994 |
| WO | WO-98/40053 | 9/1998 |
| WO | WO-99/01111 | 1/1999 |
| WO | WO-00/25769 | 5/2000 |
| WO | WO-00/32558 | 6/2000 |
| WO | WO-00/41681 | 7/2000 |
| WO | WO-01/15667 | 3/2001 |
| WO | WO-01/15681 | 3/2001 |
| WO | WO-01/15682 | 3/2001 |
| WO | WO-01/15683 | 3/2001 |
| WO | WO-01/24783 | 4/2001 |
| WO | WO-01/45676 | 6/2001 |
| WO | WO-02/02084 | 1/2002 |
| WO | WO-02/43706 | 6/2002 |
| WO | WO-02/060415 | 8/2002 |
| WO | WO-03/037296 | 5/2003 |
| WO | WO-03/072025 | 9/2003 |
| WO | WO-03/080031 | 10/2003 |
| WO | WO-03/099265 | 12/2003 |
| WO | WO-2004/037222 | 5/2004 |
| WO | WO 2004038428 A2 * | 5/2004 |
| WO | WO-2004/080447 | 9/2004 |
| WO | WO-2010/019279 | 2/2010 |

OTHER PUBLICATIONS

Bodalia et al., "A Comparison of the Pharmacokinetics, Clinical Efficacy, and Tolerability of Once-Daily Tramadol Tablets with Normal Release Tramadol Capsules," Journal of Pain and Symptom Management, vol. 25, No. 2, pp. 142-149 (2003).
Boureau, "Tramadol in Post-Herpetic Neuralgia: A Randomized, Double-Blind, Placebo-Controlled Trial," PAIN, Elsevier Sci Pub. 2003, vol. 104 (1/2):323-331.
Brooks et al., "Trazodone—A comparison of single night-time and divided daily dosage regimens," Psychopharmacology 84:1-4 (1984).
DeJong, R, "Comment on the hypoalgesic effect of tramadol in relation to CYP2D6," Pain Dig, 7, 1997, p. 245.
Desmeules, "The tramadol option," European Journal of Pain, 4, Suppl. A:15-21 (2000).
Excerpt from "Controlled Drug Delivery. Fundamentals and Applications," Second Edition, Revised and Expanded, Joseph R. Robinson, et al., Editors (1987) (68 pages).
Excerpt from "Handbook of Pharmaceutical Controlled Release Technology," Donald L. Wise, Executive Editor (2000) (80 pages).
Fabre, "Trazodone Dosing Regimen: Experience with Single Daily Administration," J. Clin. Psychiatry 51:9 (suppl.), pp. 23-26 (1990).
Fleischmann, "Tramadol for the treatment of joint pain associated with osteoarthritis: a randomized, double-blind, placebo-controlled trial," Current Therapeutic Research 62(2):113-128 (2001).
Gennaro R. Alfonso, Remington Farmacia, 19th Edition, Panamericana, Spain. 1988, pp. 2470, 2535 (in Spanish) and an English translation.
Haria et al., "Trazodone: A Review of its Pharmacology, Therapeutic Use in Depression and Therapeutic Potential in Other Disorders," Drugs & Aging 4(4):331-355 (1994).
International Search Report for International Patent Application No. PCT/CA03/01637, dated Apr. 27, 2004.
International Search Report for International Patent Application No. PCT/CA03/01638, dated Apr. 27, 2004.
Ispas-Szabo et al. (1999) "Structure-properties relationship in cross-linked high-amylose starch for use in controlled drug release" Carbohydrate Research. Pergamon. 323:163-175.
Kasper et al., "A Comparative, Randomised, Double-Blind Study of Trazodone Prolonged-Release and Paroxetine in the Treatment of Patients with Major Depressive Disorder," 21 Current Med. Res. & Opinion 8, pp. 1139-1146 (2005).
Klaschik, "Office-oriented pain therapy in cancer patients—Adequate alleviation of pain with the appropriate medication," Klinikarzt 31(9):250-256 (2002). (English abstract provided on p. 256).
Kogel, B. et al., "Involvement of metabolites in the analgesic action of tramadol," Proc. 9th World Congress on Pain, Vienna, Austria, Aug. 22-27, 1999, pp. 523.
Labopharm, Inc. Press Release dated Feb. 2, 2010 relating to FDA approval of OLEPTRO™ (4 pages).
Labopharm, Inc. Press Release dated Nov. 12, 2010 relating to ANDA Submission with Paragraph IV Certification for Generic of OLEPTRO™ (2 pages).
Lenaerts et al. "Controlled release of theophylline from cross-linked amylose tablets" Journal of Controlled Release, 15 (1991) pp. 39-46.
Lenaerts et al. "Cross-linked high amylose starch for controlled release of drugs: recent advances" Journal of Controlled Release 53 (1998) pp. 225-234.
Mateescu, "Use of Crosslinked Amylose for the Quantitative Determination of α- and β-Amylase," Lab. Enzymol., Inst. Sci. Biol., Bucharest, Rom., Biochimie 60(5), 535-7 (1978) (English Abstract provided).
Mendelson, "A Review of the Evidence for the Efficacy and Safety of Trazodone in Insomnia," J. Clin. Psychiatry 66:4, pp. 469-476 (2005).
Moon et al., "Efficacy and Tolerability of Controlled-Release Trazodone in Depression: A Large Multi-Centre Study in General Practice," 12 Current Med. Res. and Opinion 3, pp. 160-168 (1990).
Nies and Spielberg, Goodman & Gilman. Las Bases Farmacologicas de la Terapeutica. Novena Edicion. vol. I. McGraw-Hill. Interamericana. Mexico. 1996, pp. 47, 58 (in Spanish) and an English translation.
Opposition statement against Chilean Application No. 2186-2003 by La Asociacion Industrial De Laboratorios Farmaceuticos A.G. (in Spanish) and its English translation, 2003.
Opposition statement against Chilean Application No. 2187-2003 by La Asociacion Industrial De Laboratorios Farmaceuticos A.G. (in Spanish) and its English translation, 2003.
Opposition statement against Chilean Application No. 2187-2003 by Laboratorios Recalcine S.A. (in Spanish) and its English translation, 2003.
Opposition statement against Chilean Application No. 600-2007 by Asociacion Industrial de Laboratorios Farmaceuticos AG (in Spanish) and an English translation, 2007.
Opposition statement against Chilean Application No. 605-2007 by Asociacion Industrial de Laboratorios Farmaceuticos AG (in Spanish) and an English translation, 2007.
Opposition statement against Chilean Application No. 605-2007 by Laboratorios Recalcine S.A. (in Spanish) and an English translation, 2007.
Partial European Search Report for EP 04 02 4164, Aug. 9, 2006.
Roth, S.H., "Efficacy and safety of tramadol HCL in breakthrough musculoskeletal pain attributed to osteoarthritis," J. Rheumatol 1998, 25:1358-1363.

Rotzinger et al. (1998) "Trazodone is Metabolized to m-Chlorophenylpiperazine by CYP3A4 From Human Sources" Drug Metabolism and Disposition 26:572-575.

Ruoff, "Slowing the initial titration rate of tramadol improves tolerability," Pharmacotherapy 19(1):88-93 (Jan. 1999).

Ruoff, G.E., "Strategies to Control Chronic Musculoskeletal Pain: A Guide to Drug Therapy," Oct. 1999, Consultant, 39, pp. 2773-2781.

Saletu-Zyhlarz et al., "Confirmation of the Neurophysiologically Predicted Therapeutic Effects of Trazodone on Its Target Symptoms Depression, Anxiety and Insomnia by Postmarketing Clinical Studies with a Controlled-Release Formulation in Depressed Outpatients," Neuropsychobiology 2003; 48:194-208.

Search Report and Written Opinion for Intl. Application PCT/CA2006/001483, Jun. 4, 2007.

Search Report and Written Opinion for Intl. Application PCT/CA2006/001484, Jun. 8, 2007.

Stamer, "Impact of CYP2D6 genotype on postoperative tramadol analgesia," PAIN, 105(1-2):231-238 (2003).

Supplementary European Search Report for EP 06 79 0660, dated Jun. 24, 2011 (5 pages).

Uncertified translation of Japanese Patent Office Action issued on Apr. 23, 2012 for 2008-529430 which notes JP patent documents identified as B__and B__(2 pages).

Visavarungroj, N. et al., "Crosslinked Starch as a Disintegrating Agent," International Journal of Pharmaceutics 1990, vol. 62, No. 2/3, pp. 125-131.

Wilder-Smith, C.H., "Treatment of severe pain from osteoarthritis with slow-release tramadol or dihydrocodeine in combination with NSAID's: a randomized study comparing analgesia, antinociception and gastrointestinal effects," Pain, 91, 2001, pp. 23-31.

* cited by examiner

SUSTAINED DRUG RELEASE COMPOSITION

RELATED APPLICATIONS

This application is a continuation of U.S. patent application Ser. No. 11/519,189, filed Sep. 11, 2006, which claims the benefit of U.S. Provisional Patent Application Ser. No. 60/715,162, filed Sep. 9, 2005, the entire disclosures of each of which are incorporated by reference herein.

FIELD OF THE INVENTION

The present invention relates generally to a sustained release drug composition and more particularly to a sustained release drug composition, which when subdivided into smaller dosage forms, the smaller dosage forms display substantially the same drug release profile as the composition from which they were derived.

BACKGROUND

Typically, oral dosage forms for the delivery of pharmaceutically active agents or drugs release the agent during passage through the gastrointestinal tract. The part of the gastrointestinal tract to which the active agent is delivered depends in part on the type of delivery system involved. Certain delivery systems release the active substance rapidly, leading to, for example, a rapid rise to a maximum concentration of drug in the blood usually followed by a rapid decrease in concentration as the drug is cleared from the body. If the drug concentration rises and/or decreases rapidly, this may create a narrow window of time during which the drug is therapeutically effective. As a result, sustained therapeutic efficacy may require administration of multiple, sequential doses of the drug. In addition, if release of drug to the body is uncontrolled in this manner, adverse events associated with the drug may not be controllable and the drug may not be effectively delivered to the site requiring treatment.

Various compositions and dosage forms have been used to control drug release and thereby provide sustained release of active agents to provide sustained efficacy from one composition. For example, a well-known way of controlling the release of drug is to apply a coating to a solid core. For example, a polymer coating can produce a rate controlling film on the surface of the core. The release rate of the therapeutic agent can then be altered by factors including the thickness of the coating, the diffusivity of agent, through the coating, and the rate of biodegradation of the coating. If the coated dosage form is broken, or damaged, during or after administration, the coating may no longer provide an effective rate controlling film resulting in the drug being rapidly released from the core.

Drug dosing regimens, be they acute or chronic, may vary from patient to patient. Different patients can have different therapeutic responses to a given dose of drug. Further, physicians sometimes start with a smaller than recommended dose of a drug and titrate the dose upward over time to minimize, for the patient, the frequency and severity of adverse events associated with optimum blood concentrations of the drug. Alternatively, for some patients and/or drug therapies, physicians start with a high, or loading dose of drug to achieve maximum and rapid therapeutic benefit and then reduce the dose administered to maintain efficacy. Such dosing regimens require precise control over the dosage administered, which, with the right formulation, can be achieved using for example, a single tablet that may be sub-divided into subunits each having a smaller dose of the drug, where each of the subunits delivers the drug in the same manner as the tablet from which they were derived.

There is a need, therefore, for a formulation of a pharmaceutically active agent, which when sub-divided or broken into smaller dosage forms achieves substantially the same sustained release profile as the original formulation, and which conveniently permits modification of dosing regimens.

SUMMARY OF THE INVENTION

The invention provides solid, sustained drug release dosage forms that can be subdivided into smaller dosage forms. The smaller dosage forms provide substantially the same drug release kinetics as the solid dosage form they were created from. The formulations provided herein permit a recipient, a treating physician, or a person administering the drug, to conveniently create smaller dosage forms that can be used to more accurately and precisely deliver the appropriate amount of drug to the recipient.

In one aspect, the invention provides a solid, monolithic sustained release pharmaceutical composition comprising: (a) a sustained release matrix having a solvent accessible surface, wherein the matrix comprises cross-linked high amylose starch; and (b) an effective amount of at least one pharmaceutically active agent disposed within the matrix. The composition has a hardness of greater than about 100 N, for example, in the range from about 100N to about 350 N.

Such a composition, when administered to a mammal, for example, a human, achieves an effective plasma concentration, for example, a therapeutically effective plasma concentration of the active agent from at least about 1 hour to at least about 24 hours after initial administration. The composition comprises a solvent accessible surface that optionally defines a score or scores, which permits the composition to be subdivided along the score to produce at least two subunits each having a new solvent accessible surface. At least one of the resulting subunits has substantially the same release kinetics of the active agent as the intact composition from which it was derived. Furthermore, the dissolution profiles of at least one of the subunits and the composition from which it was derived have a similarity factor of at least 50%, at least 55%, at least 60%, at least 65%, at least 70%, at least 75%, and at least 80%.

In another aspect, the invention provides a solid sustained release pharmaceutical composition comprising: (a) a sustained release matrix having a solvent accessible surface, wherein the matrix comprises cross-linked high amylose starch; and (b) an effective amount of a pharmaceutically active agent disposed within the matrix The composition (i) displays substantially the same release kinetics when the composition is broken or subdivided along a score, to create a new solvent accessible surface, and/or (ii) can be divided into at least two subunits where each subunit releases the active agent with substantially the same release profile as the composition from which they were derived.

The composition has a hardness of greater than about 100 N, and, for example, has a hardness in the range from about 100 N to about 350 N. Such a composition can be monolithic in nature. The new solvent accessible surface created by dividing or breaking the original dosage form, and like the original solvent accessible surface of the original intact form, can form a barrier having membrane-like properties when exposed to an aqueous solvent.

The dissolution profiles of at least one subunit and the composition from which it was derived have a similarity factor of at least 50%, at least 55%, at least 60%, at least 65%, at least 70%, at least 75%, and at least 80%. The subunits and the intact composition from which they are derived can be designed to be bioequivalent, and each subunit can release the active agent for at least about 12 hours, about 18 hours, or at least 24 hours.

The compositions described herein comprise from about 15% to about 60% by weight of the active ingredient and from about 15% to about 85% by weight of a controlled release excipient that defines the sustained release matrix, from about 20% to about 50% by weight of the active ingredient and from about 20% to about 50% by weight of the controlled release excipient, and from about 35% to about 50% by weight of the active ingredient and from about 20% to about 50% by weight of the controlled release excipient.

It is contemplated that a number of different controlled release excipients may be useful in the practice of the invention. The controlled release excipients comprise cross-linked high amylose starch. In certain embodiments, the cross-linked high amylose starch is cross linked with phosphorus oxychloride and/or comprises hydroxypropyl side chains. In certain other embodiments, the cross-linked high amylose starch comprises between about 65% and about 75% by weight of amylose and is cross-linked with phosphorus oxychloride. One preferred cross-linked high amylose starch useful in the practice of the invention is known as CONTRAMID® cross-linked, high amylose starch, available commercially from Labopharm, Inc., Laval, Canada.

It is contemplated that a number of different pharmaceutically active agents can be incorporated into the compositions and dosage forms of the invention. Such active agents can include, for example, antidepressants, for example, trazodone, and analgesics, for example, tramadol and acetaminophen or combinations thereof. It is contemplated that one, two, three or more active agents can be incorporated into the formulations described herein.

In addition, the sustained release pharmaceutical composition optionally includes one or more pharmaceutical additives. Exemplary pharmaceutical additives include binding agents (for example, hydroxypropylmethylcellulose), solubilizing agents (for example, povidone or cetylpyridinium chloride), acidifying agents (for example, alginic acid), pore forming agents (for example, sucrose), lubricants (for example, sodium stearyl fumarate), and glidants (for example, colloidal silicon dioxide).

The sustained release pharmaceutical composition can be formulated into a variety of shapes and forms such as tablets and caplets suitable for oral administration. In one embodiment, the invention provides a caplet. Such tablets and caplets can be scored on one or both sides, and/or have multiple scores.

Also provided are methods of making the formulations described herein as well as methods of using such formulations.

BRIEF DESCRIPTION OF THE DRAWINGS

The invention is illustrated but is not limited by the annexed drawings, in which.

DETAILED DESCRIPTION

Figure 1:
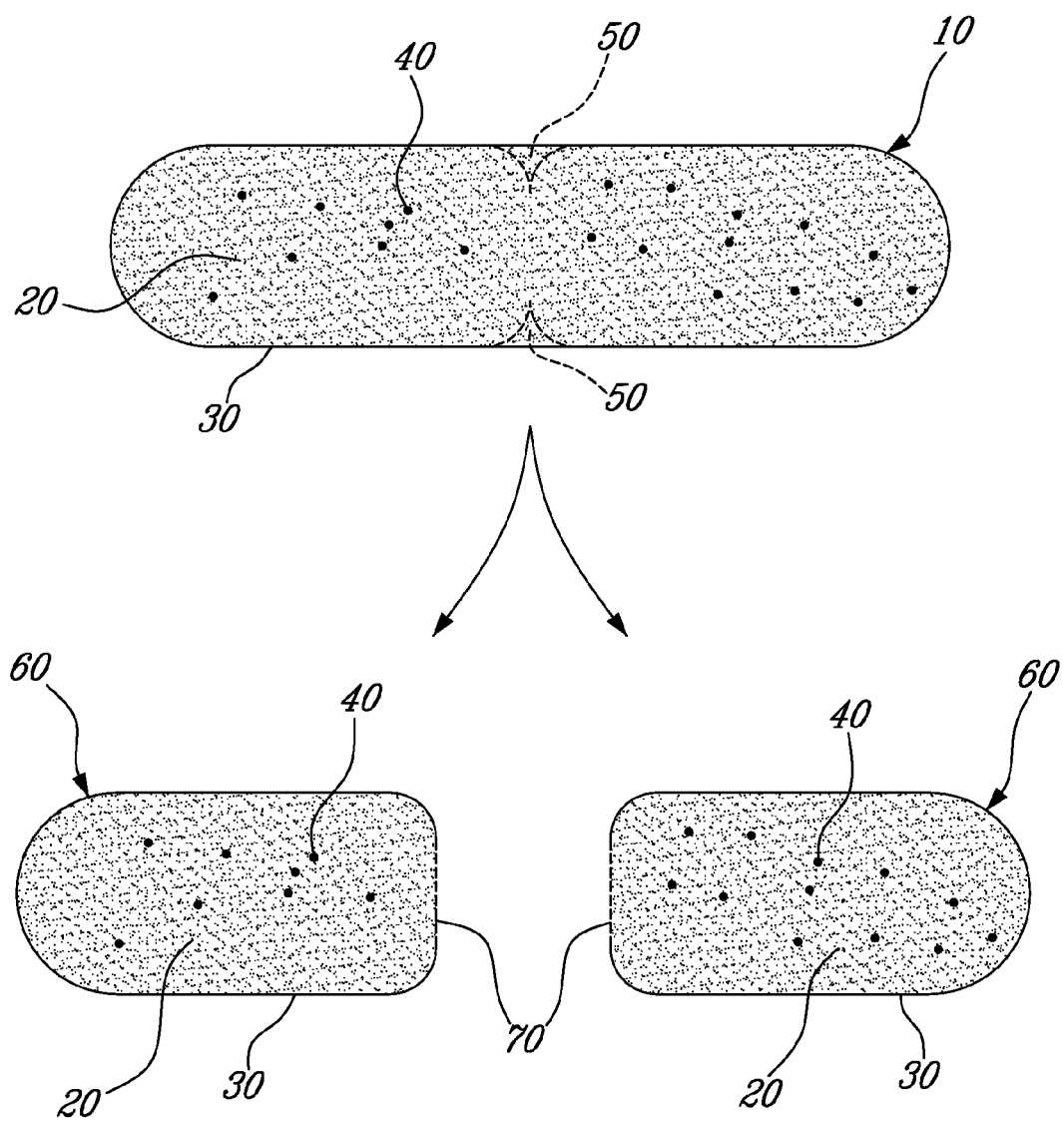
FIG. 1 is a schematic representation of an exemplary formulation of the invention.

The invention is based, in part, upon the discovery that it is possible to formulate a sustained release composition, which when sub-divided, e.g., broken or separated into subunits or smaller dosage forms, at least one of the resulting subunits or smaller dosage forms has substantially the same drug release profile as the original intact composition from which it was derived. Such a sustained release composition, whether subdivided or intact, provides a rate of release of active agent that is controlled over a period of time up to about 12 hours, up to about 18 hours, or up to about 24 hours, or more. After administration of such a sustained release composition, the drug plasma concentration of a patient may be controlled, e.g., up to 12 hours, up to 18 hours, and 24 hours. This discovery was surprising because if sub-divided (broken or separated into subunits), sustained or controlled release compositions can lose their sustained release properties, i.e., the subunits deliver the active agent in a rapid and uncontrolled fashion.

Accordingly, in one aspect the invention provides a solid, monolithic sustained release pharmaceutical composition comprising: (a) a sustained release matrix having a solvent accessible surface, wherein the matrix comprises cross-linked high amylose starch; and (b) an effective amount of at least one pharmaceutically active agent disposed within the matrix. The composition has a hardness of greater than about 100 N, for example, in the range from about 100N to about 350 N.

As used herein, the term "effective amount" can include therapeutically effective amounts and amounts suitable for titration regimens and the like, where, for example, multiple tablets or subdivided tablets need to be administered to an individual to achieve a maximum therapeutic efficacy with minimizing adverse effects.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce an amount at a reasonable benefit/risk ratio applicable to such treatment.

In another aspect, the invention provides a solid sustained release pharmaceutical composition comprising: (a) a sustained release matrix having a solvent accessible surface, wherein the matrix comprises cross-linked high amylose starch; and (b) an effective amount of a pharmaceutically active agent disposed within the matrix The composition (i) displays substantially the same release kinetics when the composition is sub-divided by breaking or fracturing to create a new solvent accessible surface, and/or (ii) can be divided into at least two subunits where each subunit releases the active agent with substantially the same release profile as the composition from which it was derived.

These formulations may be monolithic in nature. As used herein, the term "monolithic" is understood to mean a composition that releases an active agent in a substantially uniform fashion, with the composition dissolving or disintegrating substantially uniformly, rather than in layers.

The foregoing compositions have hardness of greater than about 100 N. The compositions typically have a hardness in the range from about 110 N to about 350 Accordingly, the compositions optionally can have a hardness of 110 N, 120N, 140N or higher. Preferred hardnesses range from about 100 N to about 180N, or from 110N to about 140N, or about 140 N to about 180 N. For example, the hardness may vary depending on the size of the tablet, e.g. a smaller tablet may have a hardness of about 100 N to about 140 N; a larger tablet may have a hardness of about 220 N to 260 N. As used herein, the term "hardness" is used to describe the diametral breaking strength as measured by conventional pharmaceutical hardness testing equipment. Preferably, such compression is performed in a single process.

The sustained release matrices include a controlled release excipient. The composition comprises from about 15% to about 60% by weight pharmaceutically active agent, and from about 15% to about 85% by weight percent of a controlled release excipient. The controlled release excipient, when orally administered to a mammal, for example, a person, permits the pharmaceutically active agent to achieve and/or maintain effective and/or controlled plasma concentrations, for example, an effective plasma concentration for up to about 24 hours after initial administration. Such release kinetics are substantially the same when an intact composition, e.g., a tablet is broken, separated or sub-divided into subunits.

As shown in FIG. 1, an exemplary solid sustained release composition 10 includes (i) a sustained release matrix having an interior or core 20 and a solvent accessible surface 30, and (ii) a pharmaceutically active agent 40 disposed therein. The sustained release matrix includes a controlled release excipient, such as cross-linked high amylose starch. When the composition, such as a solid dosage form, is fractured or divided, to produce subunits 60, each subunit contains a portion of the original solvent accessible surface 30 and a newly exposed solvent accessible surface 70. Without wishing to be bound by theory, the controlled release excipient, e.g., cross-linked high amylase starch, may form a membrane e.g. a semipermeable membrane, or barrier layer, which may be, for example, over, on, or constitute part of the solvent accessible surface (30 and 70). Such a barrier may contribute to substantially stable release kinetics of the active agent in the sub-divided or intact forms.

The intact solid sustained release composition 10 optionally comprises one or more scores 50, shown in phantom in FIG. 1. The scores can be used to guide the subdivision of the intact tablet. Although FIG. 1 shows a tablet with two adjacent scores, however, it is contemplated that the tablet can contain more scores if more than two subunits are desired.

Accordingly, the invention provides a sustained release solid dosage form comprising cross-linked high amylose starch and a pharmaceutically active agent, wherein the solid dosage form can be separated into subunits, with each subunit having substantially the same sustained release properties as the intact or unbroken solid dosage form. Dosage forms may be bisected, e.g., divided into two substantially equal pieces, or may be divided into other fractional sections, e.g., thirds or fourths. Dosage forms may also be divided into unequal sections, e.g., one-third/two-thirds.

In vitro dissolution profiles of intact and separated sustained formulations as described herein may be compared using fit factors or other mathematical comparisons. Such fit factors are known to those skilled in the art and are used to predict bioequivalency of different dosage forms. The fit factor $f_1$ represents relative error between two curves, or in other words, the mean relative difference on all measured points. Fit factor $f_1$ is sometimes referred to as the difference factor. The mean relative difference for each sample point should be between about 0 to about 15% for bioequivalence. In some embodiments, compositions and/or formulations may have a similarity factors between an intact dosage form and subunits of the intact dosage form of less than about 15%, less than about 10%, or less than about 7%. The fit factor $f_2$ is a logarithmic transformation of the mean of squares differences between two curves. Fit factor $f_2$ is sometimes referred to as the similarity factor. The similarity factor should be between about 50% and about 100% for bioequivalence, e.g., between the subunit forms and intact dosage forms. In some embodiments, compositions and/or formulations can have similarity factors between an intact dosage form and the subunits derived from the intact dosage form of at least 50%, at least 55%, at least 60%, at least 65%, at least 70%, at least 75%, and at least 80%.

The formulations described herein can provide rise in plasma concentrations of the active ingredient, which thereafter remain relatively and substantially stable for at least 10, at least 12, at least 18, or at least 24 hours or more, regardless of whether the dosage form is separated into subunits or is in an intact form. The plasma concentration between one hour and 24 hours may remain within about 45% of the mean plasma concentration, more preferably between about 30% of the mean, and most preferably between about 15% of the mean plasma concentration. In certain formulations, after an initial rapid release of the active agent, within an hour of ingestion the active agent is released in vivo with approximately zero order kinetics for at least about 24 hours, leading to plateau plasma concentrations.

Dosages in a particular sustained release formulation can vary to a large extent depending on required needs of the patient, and the specific requirements of the treating physician. For example, the dosage of any compositions of the present invention will vary depending on the symptoms, age and body weight of the patient, the nature and severity of the disorder to be treated or prevented, the route of administration, and the form of the subject composition. Dosages for the compositions of the present invention may be readily determined by techniques known to those of skill in the art or as taught herein. The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

Specific sustained dosages can be tailored using the dosage forms by breaking the dosage forms disclosed herein into substantially similar but smaller doses having substantially similar sustained release profiles. For example, smaller doses may be useful for patients lighter in weight and/or for paediatric use. Alternatively, one dosage may be provided, but in a smaller form that may be more acceptable to a patient. For example, a patient may be able to divide a dosage into easier-to-swallow components while still maintaining the sustained release properties of the dosage form. The ability to alter dosage on a patient by patient basis with one dosage form may also be convenient for, e.g., a physician or a pharmacist.

For some patients, a typical recommended dose may be larger than what is needed, increasing the chance of adverse effects. For example, patients taking tramadol, reported adverse reactions include dizziness, nausea and constipation. Reported adverse effects for trazodone formulations include dizziness, dry-mouth, nervousness and fatigue. Patients taking betahistidine have reported gastric upset, nausea and headache.

One approach for decreasing adverse effects is dose titration. For example, for patients that do not require an immediate response, a dose that is about one-fourth to one-half the recommended dose may be initially administered and over a course of a time, e.g., two to four weeks, the dose may be titrated or increased until the desired effect is obtained. For acute conditions, titration can occur over the course of days, rather than weeks. The disclosed dosage forms may used in such dose titration regimens, for example, by dividing an intact form into sub-sections that can be taken individually for smaller doses and then taken in larger sub-sections or intact forms for larger doses. Dose titration is often used, for example, in the administration of analgesics such as opioids to achieve pain relief while maintaining an acceptable level of adverse side effects.

The disclosed dosage forms may used in such dosage regimens that start with, e.g., the recommended dose, and subsequently have reduced dosages according to the patient's needs. For example, such a regimen may be accomplished by administring an intact dosage form as disclosed herein and then dividing an intact form into subunits, each of which can be taken individually for smaller doses.

The composition according to the invention is normally prepared in the form of a tablet. Although the tablet can adopt a wide variety of shapes as is well known to those skilled in the art, the preferred shape is a caplet. Such caplets may be formed, for example, with composition including a controlled release excipient and at least one active agent and using upper and lower punches set in a tableting machine as is known in the art. In some embodiments, tablets may include a coating, such as, for example, an inert coating containing a colorant. Suitable coatings include, for example, aqueous film coating polymers such as polyvinyl alcohol, talc, macrogel and the like, and mixtures thereof. Suitable colorants include, for example, iron oxides, lakes, natural colorants and other colorants known to those skilled in the art. Preferably, such a coating does not affect the release kinetics, e.g. dissolution performance of a dosage form when intact or when subdivided.

Figure 5:
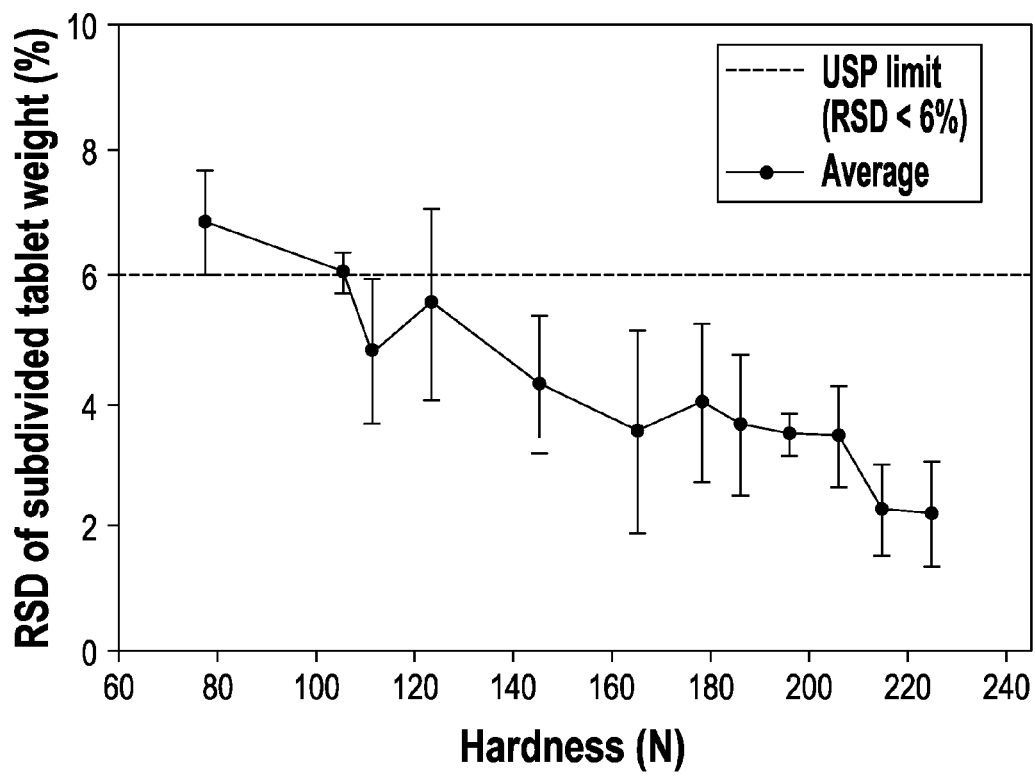
FIG. 5 is a graph illustrating the test for uniformity of mass on an exemplary tablet formulation containing 150 mg trazodone where a hardness of 111 N is required to achieve a relative standard deviation (RSD) of less than 6% as required by the U.S.P.

In some embodiments, the dosage forms, e.g., tablets, may be scored. Preferably, scored tablets or un-scored tablets are broken with high breaking accuracy thereby ensuring matching or proportional release profiles from each resultant subdivision. Breaking accuracy may determined for example, by evaluating the mass uniformity of separated, e.g., bisected, parts of the same tablet. The mass uniformity of a tablet may be determined in terms of relative standard deviation (RSD) from the mean mass of tablet sections using the U.S.P. test limit of uniformity (RSD below 6%). FIG. 5 indicates, for the exemplary formulation as described in Example 2, hereinbelow, that for such a formulation, the minimum tablet hardness needed for mass uniformity with an RSD below 6% is about 110 N.

Scoring may have varying depths, e.g., from about 0% (e.g., no scoring) to about 95% of the tablet cup depth. Each tablet may have one, two, or multiple scores, and/or scoring on one or both sides of the tablet. As can be seen in Example 1, hereinbelow, scoring does not substantially affect the release profiles of the tablets when intact or when broken along the score.

The formulations may have in vitro profiles as described in the Examples hereinbelow. The in vitro release profiles can be measured using the U.S.P. paddle method (apparatus type II as described in U.S.P. XXVI) at 150 revolutions per minute, at 37±0.5° C., in 900 mL of hydrochloride/sodium chloride pH 1.2 solution (acid stage) followed after one hour by 900 mL of sodium phosphate monobasic buffer pH 6.0 (buffer stage). In some embodiments, formulations may have release kinetics, whereby, when tested by the foregoing method, not more than about 30% of the active ingredient is released by 1 hour after initiation of the experiment, about 35% to 55% of the active ingredient is released by 6 hours, not more than about 80% of the active ingredient is released by 12 hours, and/or not less than about 80% of the active ingredient is released by 24 hours.

Formulations contemplated herein may reach steady-state, for example, on-average, within a normal population, after about the fourth administration. The peak-to-trough ratio produced by such formulations at steady-state may be about 60% to about 100%.

The formulations described herein are particularly useful in the delivery of pharmaceutically active agents and their derivatives. Derivatives include pharmaceutically acceptable pro drugs, metabolites, salts and esters, or the like. For example, the term "pharmaceutically-acceptable salts" is art-recognized and refers to the relatively non-toxic, inorganic and organic acid addition salts of compounds, including, for example, those contained in compositions of the present invention.

The term "pharmaceutically active agent" refers to any chemical moiety that is a biologically, physiologically, or pharmacologically active substance that acts locally or systemically in a subject. Examples of pharmaceutically active agents, also referred to herein as "drugs," are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

Compositions and formulations contemplated herein may include one or more pharmaceutically active agents. For example, a composition may include two, three or more different pharmaceutically active agents.

The pharmaceutically active substance of the invention can vary widely with the purpose for the composition. It is contemplated that one or a plurality of different pharmaceutically active agents are included in the formulations described herein. Non-limiting examples of broad categories of useful pharmaceutically active agents include the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and pro-drugs.

More specifically, non-limiting examples of useful pharmaceutically active substances include the following therapeutic categories: analgesics, such as nonsteroidal anti-inflammatory drugs, opiate agonists and salicylates; antihistamines, such as $H_1$-blockers and $H_2$-blockers; anti-infective agents, such as anthelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, antiretroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, β-blocker sympatholytics, sympathomimetics, and adrenergic agonist sympathomimetics; cardiovascular agents, such as antianginals, β-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-COA reductase inhibitors, antilipemics, inotropes, cardiac glycoside inotropes, and thrombolytic agents; dermatological agents, such as antihistamines, anti-inflammatory agents, corticosteroid anti-inflammatory agents; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; sychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful pharmaceutically active agents from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, tramadol, hydromorphone, and morphine; (3) salicylate analgesics, such as aspirin; (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous β-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) α-blocker sympatholytics, such as prazosin; (34) 9-blocker sympatholytics, such as atenolol; (35) adrenergic agonist sympathomimetics, such as albuterol and dobutamine; (36) cardiovascular agents, such as aspirin; (37) i-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenyloin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) a blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as aminone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal anti-infectives, such as amphotericin B, clotrimazole, miconazole, and nystatin; (61) antiviral anti-infectives, such as acyclovir; (62) antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine, trazodone, and ticlopidine; (102) anticonvulsants, such as carbamazepine, gabapentin, lamotrigine, phenyloin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, tramadol, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfuram, naltrexone, and nicotine; (125) withdrawal substance abuse agents, such as bromocriptine; (126) minerals, such as iron, calcium, and magnesium; (127) vitamin B compounds, such as cyanocobalamin (vitamin $B_{12}$) and niacin (vitamin $B_3$); (128) vitamin C compounds, such as ascorbic acid; (129) vitamin D compounds, such as calcitriol, and (130) histiamine type drugs such as betahistine hydrochloride.

In some embodiments, compositions disclosed herein include more than about 15% pharmaceutically active ingredient by weight, for example between about 15% and about 60%, or between about 20% and about 60%, or between about 20% and about 55% by weight. In other embodiments, compositions contemplated herein may include more than about 15% weight controlled release excipient such as cross-linked high amylose starch, for example, between about, 15% and about 85%, or about 20% and about 85%, or about 20% and about 60%, or about 20% and about 50%, or about 30% and about 50% by weight. The composition according to the invention preferably comprise from about 15% to about 50% by weight, more preferably, from about 25% to about 50% active ingredient and from about 20% to 60% by weight, more preferably from about 25% to about 50% by weight of controlled release excipient. In a particular embodiment, this invention is directed to a composition comprising about 5% to about 50% by weight of active ingredient and about 30% to about 50% by weight of cross-linked high amylose starch.

Controlled release excipients contemplated herein may vary to a large extent as is well known to one skilled in the art, provided that a formulation including an excipient has the disclosed release properties and/or therapeutic action. Controlled release excipients may include cross-linked starches, hydrogels, celluloses, and/or polymers, and other controlled release excipients known to those skilled in the art.

In one embodiment, the controlled release excipient preferably comprises a cross-linked high amylose starch, for example, where the cross-linked high amylose starch is cross-linked with phosphorus oxychloride and/or comprises hydroxypropyl side chains. A suitable excipient has been developed by and is available commercially from Labopharm, Inc., Laval, Canada, under the trademark CONTRAMID®. The synthesis of the CONTRAMID® excipient is described, for example, in U.S. Pat. No. 6,607,748, hereby incorporated by reference in its entirety for all purposes. Compositions contemplated herein may include cross-linked high amylose starch together with one or more additional controlled release excipients.

Cross-linking of starch represents a powerful method for modifying starch. Usually, starch granules are cross-linked to increase resistance of the paste to shear or heat. Such chemically cross-linked starches provide a desirable smooth texture and possess viscosity stability throughout processing operations and normal shelf life. In some embodiments, cross-linked high amylose starch as contemplated herein may be gelatinized after cross-linking. In a preferred embodiment, cross-linking high amylose starch may include additional chemical modification (e.g., hydroxypropylation) prior to gelatinization.

The cross-linking of high amylose starch may be realized according to procedures described in the art. For example, cross-linking of amylose can be carried out in the manner described in Mateescu [BIOCHEMIE 60: 535-537 (1978)] by reacting amylose with epichlorohydrin in an alkaline medium. In the same manner, starch can also be cross-linked with a reagent selected from the group consisting of epichlorohydrin, adipic acid anhydride, sodium trimetaphosphate and phosphorous oxychloride or other cross-linking agents including, but not limited to, 2,3-dibromopropanol, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis(hydroxymethyl) ethyleneurea, mixed carbonic-carboxylic acid anhydrides, imidazolides of carbonic and polybasic carboxylic acids, imidazolium salts of polybasic carboxylic acids, and guanidine derivatives of polycarboxylic acids. The reaction conditions employed will vary with the type and amount of the cross-linking agent that is used, as well as the base concentration, amount and type of starch.

It is contemplated that starches containing more than about 40% w/w amylose can be used to form cross-linked high amylose starch, e.g., pea and wrinkled pea starch, bean starch, hybrids or genetically modified tapioca or potato starch, or any other root, tuber or cereal starch. Preferably, high amylose starch containing about 70% w/w amylose is used as the base material. For example, high amylose starch, Cerestar AmyloGel 03003 (Cerestar U.S.A. Inc.), may be used. In certain formulations, the excipient comprises cross-linked high amylose starch comprising between about 65% and about 75% by weight amylose cross-linked with phosphorus oxychloride.

The pharmaceutical composition according to the invention optionally can also comprise pharmaceutically acceptable additives. Such additives can include, for example, sugars, such as lactose, glucose and sucrose; other starches, such as corn starch and potato starch; cellulose, and its derivatives, such as sodium carboxymethyl cellulose, ethyl cellulose and cellulose acetate; powdered tragacanth; malt; gelatin; talc; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; and other non-toxic compatible substances employed in pharmaceutical formulations. Such additives may also include colorants and/or taste-masking additives.

For example, the compositions disclosed herein may include any one of a mixture of a binding agent, a solubilizing agent, an acidifying agent, a pore forming agent, a lubricant, a glidant, as is well known to those skilled in the art. Preferred pharmaceutical additives that are used in providing a composition according to the invention may include, for example, binding agents that include hydroxypropylmethylcellulose, hydroxypropylcellulose, hydroxyethylcellulose, methylcellulose, dicalcium phosphate, calcium phosphate, microcrystalline cellulose, start or the like, solubilizing agents such as povidone, cetylpyridinium chloride, or the like, acidifying agents such as alginic acid, citric acid, succinic acid, bile acid or the like, a pore forming agent such as sucrose, lactose, mannitol or the like, lubricants such as sodium stearyl fumarate, magnesium stearate, calcium stearate, stearic acid, hydrogentated vegetable oils or the like and/or glidants such as colloidal silicon dioxide, talc or the like. Other additives well known to those skilled in the art may of course be included in the composition according to the invention without departing from the scope and spirit of the present invention.

For example, in one embodiment, the composition may comprise about 10% to 50% by weight active ingredient, for example, tramadol, acetaminophen, betahistine, about 20% to 60% by weight cross-linked high amylase starch (for example, CONTRAMID® cross-linked high amylose starch), about 10% to 25% by weight hydroxypropylmethylcellulose, about 1% to 5% by weight sodium stearyl fumarate, and up to about 1 weight percent colloidal silicon dioxide.

In an exemplary formulation protocol for producing a 5 kg batch of an exemplary sustained release formulation containing trazodone, CONTRAMID® excipient, hydroxypropylmethyl cellulose, trazodone HCl and sodium stearyl fumarate are individually weighed and sifted through a 30 mesh filter. Collodial silicon dioxide is weighed and pre-blended with CONTRAMID®, sifted through a 30 mesh filter, and blended for 10-30 seconds, for example, 15 seconds to produce d pre-blend. Hydroxypropylmethylcellulose, trazodone and the Contramid®-colloidal silicon dioxide pre-blend, are combined and blended for 5-10 minutes, for example, 7 minutes, to produce a bulk blend. A small portion of the resulting bulk blend is combined with the sodium stearyl fumarate and blended for 20-60 seconds, for example, 30 seconds. The resulting sodium stearyl fumarate blend is combined with the residual bulk blend, and the resulting mixture blended for about 2-6 minutes, for example, 4 minutes. The final blend is compressed into tablets using a compression pressure of 27 kN. Caplets are formed using a caplet standard concave punch.

The invention will now be illustrated by means of the following examples which are given for the purpose of illustration only and without any intention to limit the scope of the present invention.

EXAMPLES

Example 1

A sustained release 300 mg trazodone containing formulation (denoted Formulation 1) was prepared having the composition set forth in TABLE 1.

TABLE 1

Formulation 1

| Ingredients | Tablet (mg) | Tablet % |
|---|---|---|
| CONTRAMID ® excipient | 200 | 32.1 |
| Trazodone HCl | 300 | 48.2 |
| Hydroxypropylmethylcellulose K100M | 100 | 16.1 |
| Colloidal silicon dioxide | 3 | 0.5 |
| Sodium stearyl fumarate | 9 | 1.4 |
| Opadry II, Pink 85F94306 | 10.4 | 1.7 |
| Total | 622.4 | 100 |

Formulation 1 was compressed into tablets and analyzed. The in vitro release kinetics of the intact dosage form and subdivided (bisected) dosage forms created by breaking the intact dosage form into two were measured as follows.

Figure 2:
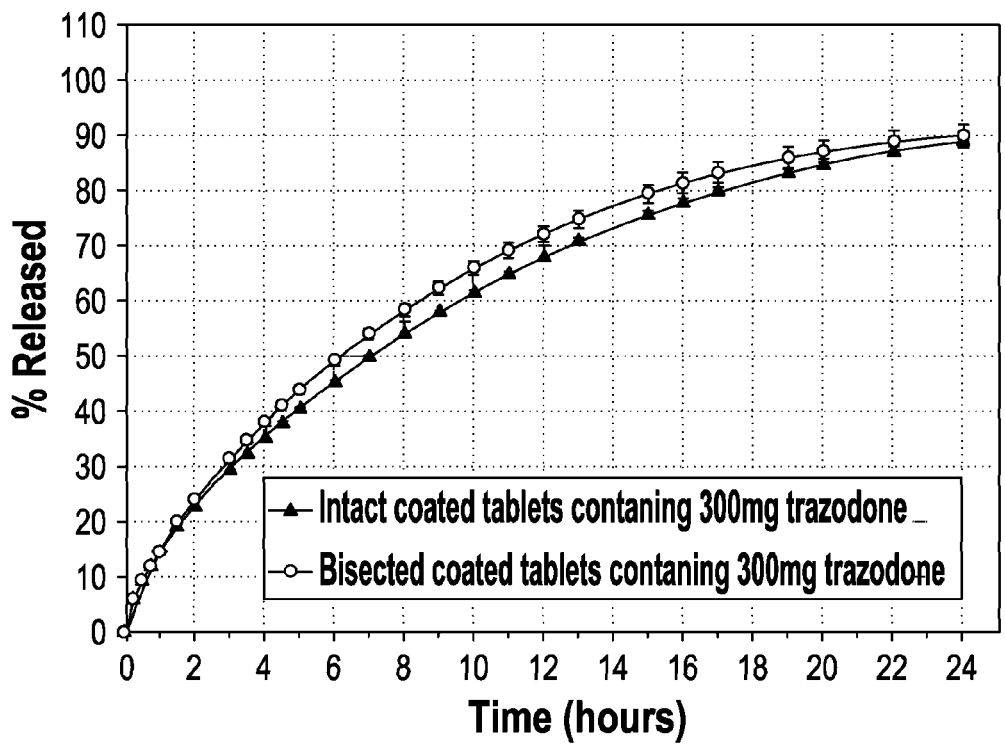
FIG. 2 is a graph illustrating the in vitro dissolution profile of an intact tablet (▲) compared to a bisected tablet (○) of an exemplary 300 mg formulation of trazodone.

Briefly, the in vitro release kinetics of Formulation 1 were measured using the U.S.P. paddle method (apparatus type II as described in U.S.P. XXVI) at 150 revolutions per minute, at 37±0.5° C., in 900 mL of hydrochloride/sodium chloride pH 1.2 solution (acid stage) followed after one hour by 900 mL of sodium phosphate monobasic buffer pH 6.0 (buffer stage). The in vitro dissolution profiles, as shown in FIG. 2, show that in this formulation, the release profiles of both the intact and bisected tablet have a similarity factor of 73.9 and a difference factor of 6.1.

Figure 3:
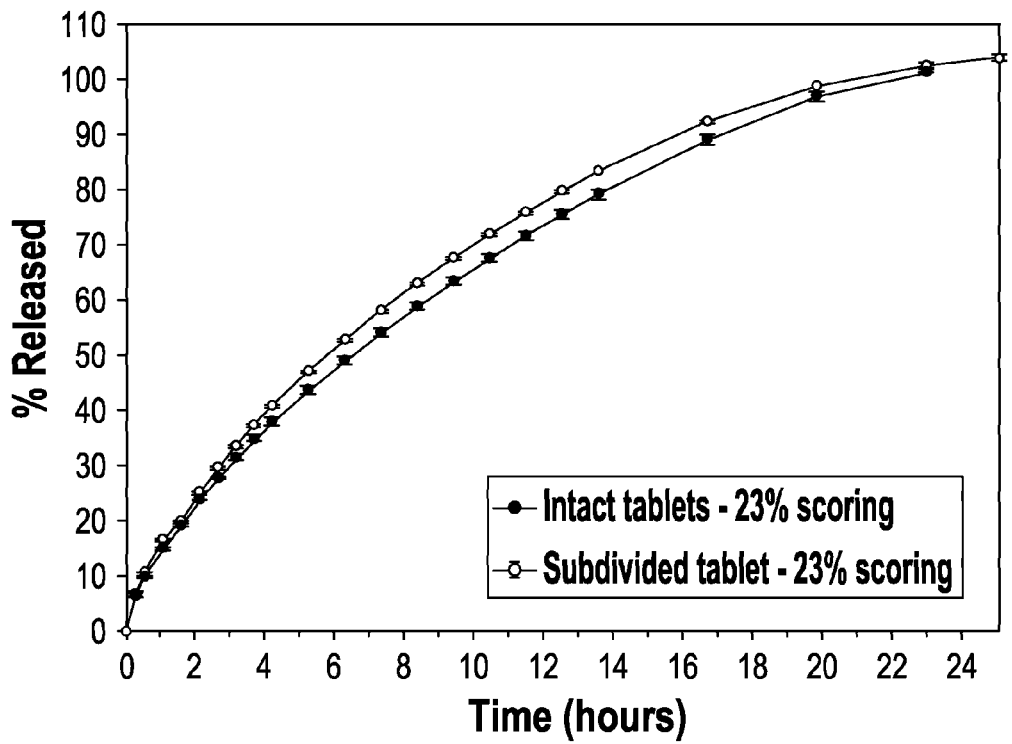
FIG. 3 is a graph illustrating the in vitro dissolution profile of an intact tablet of an exemplary formulation containing 300 mg trazodone (●) with a bisect depth score of 23% of the tablet cup depth and a subdivided tablet (○) derived from an intact tablet with the same scoring.
Figure 4:
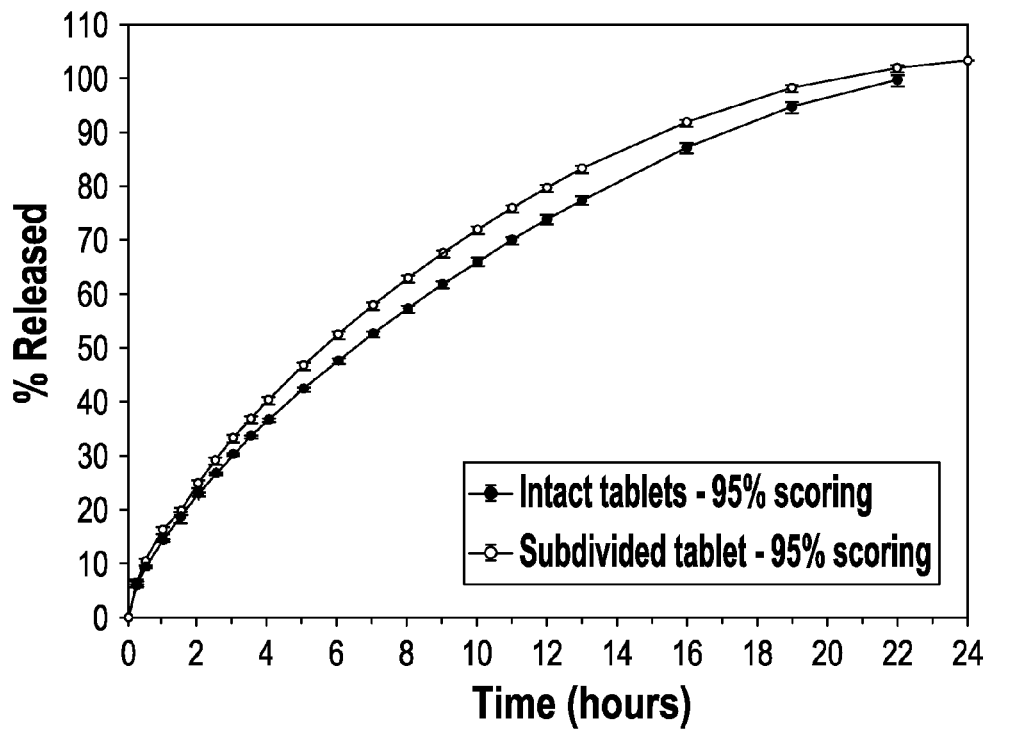
FIG. 4 is a graph illustrating the in vitro dissolution profile of an intact tablet of an exemplary formulation containing 300 mg trazodone (●) with a bisect depth score of 95% of the tablet cup depth and a subdivided tablet (○) derived from an intact tablet with the same scoring.

In addition, the effect of different score depths on release kinetics were measured. The in vitro release kinetics of two forms of the tablet having 23% scoring and 95% scoring are shown in FIGS. 3 and 4, respectively. FIGS. 3 and 4 demonstrate that the in vitro release profile of this formulation (either of the intact tablet or the subdivided tablet created by breaking the intact tablet along the score) is not substantially affected by scoring depth.

Example 2

A sustained release 150 mg trazodone containing formulation (denoted Formulation 2) was prepared having the composition set forth in TABLE 2.

TABLE 2

Formulation 2

| Ingredients | Tablet (mg) | Tablet % |
|---|---|---|
| CONTRAMID ® excipient | 252 | 46.8 |
| Trazodone HCl | 150 | 27.8 |
| Hydroxypropylmethylcellulose K100M | 126 | 23.4 |
| Colloidal silicon dioxide | 3 | 0.5 |
| Sodium stearyl fumarate | 8 | 1.5 |
| Total | 540 | 100 |

Formulation 2 was compressed into tablets. Mass uniformity testing on this formulation using the U.S.P. test limit of uniformity to achieve an RSD below 6% indicates that the minimum tablet hardness needed to achieve mass uniformity is about 110N (see, FIG. 5).

Figure 6:
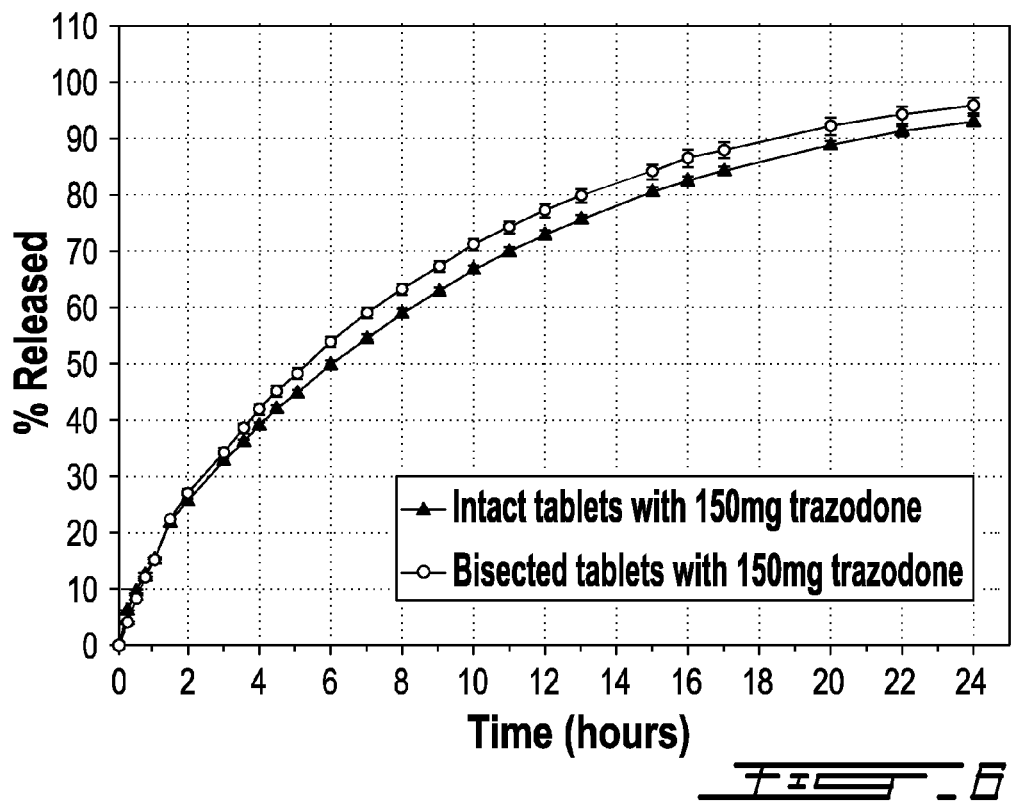
FIG. 6 is a graph illustrating the in vitro dissolution profile of an intact tablet (▲) compared to a bisected tablet (○) of an exemplary 150 mg formulation of trazodone.

The in vitro release kinetics of the intact dosage form and subdivided (bisected) dosage forms created by breaking the intact dosage form into two were measured as described in Example 1. The in vitro dissolution profiles, as shown in FIG. 6, show that in this formulation, the release profiles for both the intact and bisected tablet have a similarity factor of 73.4 and a difference factor of 6.4.

Example 3

A sustained release 300 mg tramadol containing formulation (denoted Formulation 3) was prepared having the composition set forth in TABLE 3.

TABLE 3

Formulation 3

| Ingredients | Tablet (mg) | Tablet % |
|---|---|---|
| CONTRAMID ® excipient | 200 | 32.7 |
| Tramadol HCl | 300 | 49.0 |
| Hydroxylpropylmethyl cellulose K100M | 100 | 16.3 |
| Colloidal silicon dioxide | 3 | 0.5 |
| Sodium stearyl fumarate | 9 | 1.5 |
| Total | 612 | 100 |

Figure 7:
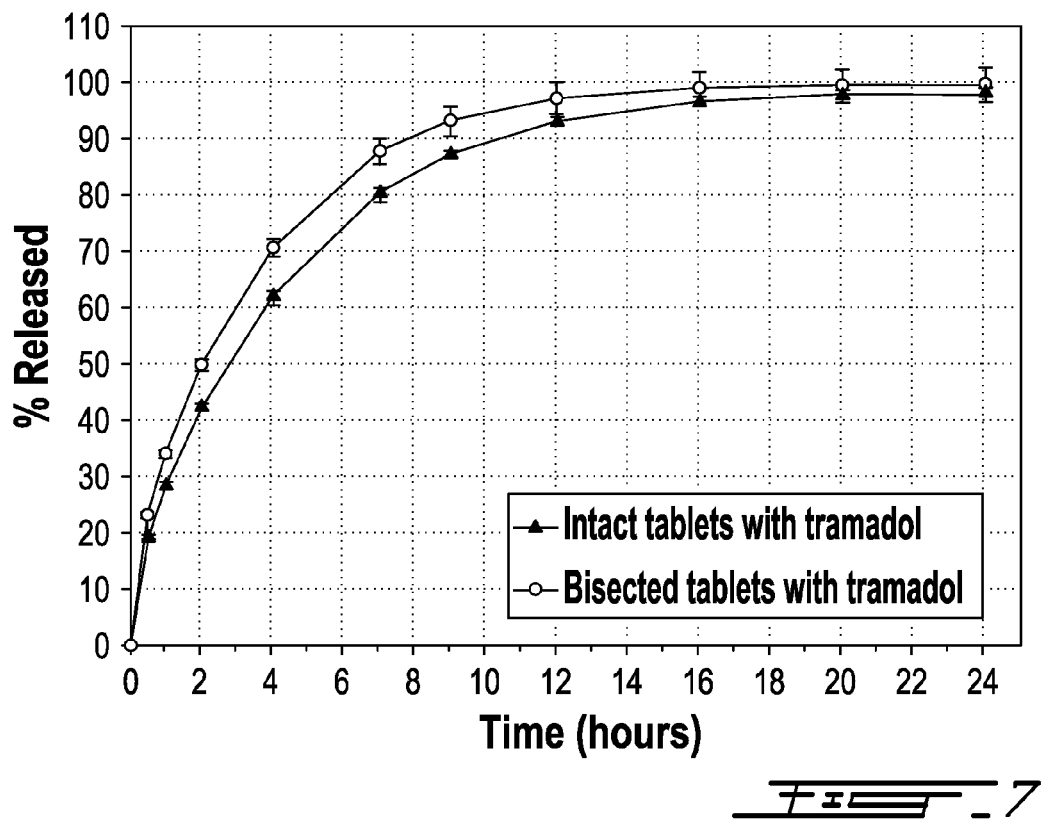
FIG. 7 is a graph illustrating the in vitro dissolution profile of an intact tablet (▲) compared to a bisected tablet (○) of an exemplary 300 mg formulation of tramadol.

The above formulation was compressed into tablets. The in vitro release kinetics of the intact dosage form and subdivided (bisected) dosage forms created by breaking the intact dosage form into two were measured as follows. Briefly, the in vitro release kinetics of the intact and bisected tablets were measured using the U.S.P. basket method (apparatus type I as described in U.S.P. XXVI) at 100 revolutions per minute, at 37±0.5° C., in 900 mL of sodium phosphate monobasic buffer pH 6.8. The in vitro dissolution profiles, as shown in FIG. 7, show that in this formulation, the release profiles for both the intact and bisected tablet have a similarity factor of 58.3 and a difference factor of 14.2.

Example 4

A sustained release 300 mg acetaminophen containing formulation (denoted Formulation 4) can be prepared having the composition set forth in TABLE 4.

TABLE 4

Formulation 4

| Ingredients | Tablet (mg) | Tablet % |
|---|---|---|
| CONTRAMID ® excipient | 200 | 32.1 |
| Acetaminophen | 300 | 48.2 |
| Hydroxylpropylmethyl cellulose K100M | 100 | 16.1 |
| Colloidal silicon dioxide | 3 | 0.5 |
| Sodium stearyl fumarate | 9 | 1.4 |
| Total | 612 | 100 |

It is contemplated that with this formulation, when compressed into tablets, the intact and bisected dosage forms will display substantially similar in vitro release kinetics.

Example 5

A sustained release 48 mg betahistine containing formulation (denoted Formulation 5) can be prepared having the composition set forth in TABLE 5.

TABLE 5

Formulation 5

| Ingredients | Tablet (mg) | Tablet % |
|---|---|---|
| CONTRAMID ® excipient | 168 | 54.90 |
| Betahistine HCl | 48 | 15.69 |
| Hydroxylpropylmethyl cellulose K100M | 84 | 27.45 |
| Colloidal silicon dioxide | 1.5 | 0.49 |
| Sodium stearyl fumarate | 4.5 | 1.47 |
| Total | 306 | 100.00 |

It is contemplated that with this formulation, when compressed into tablets, the intact and bisected dosage forms will display substantially similar in vitro release kinetics.

INCORPORATION BY REFERENCE

The entire disclosure of each of the patent and scientific documents referred to herein is incorporated by reference for all purposes.

EQUIVALENTS

Although the present invention has been illustrated by means of preferred embodiments thereof, it is understood that the invention intends to cover broad aspects thereof without departing from the spirit and scope of the invention as defined in the appended claims.

What is claimed is:

1. A solid, monolithic sustained release pharmaceutical composition having an outer surface, the composition comprising:
   a. a sustained release matrix having a solvent accessible surface, the matrix comprising from about 20% to about 60% by weight of cross-linked high amylose starch; and
   b. an effective amount of at least one pharmaceutically active agent disposed within the matrix,
   the composition having a hardness in the range of from about 100 N to about 350 N, and the outer surface of the composition defining a score that permits the composition to be fractured along the score to produce at least two subunits, wherein at least one of the subunits and the composition from which it was derived have substantially the same release kinetics of the active agent disposed therein, and wherein at least one of the subunits created by fracturing the composition has a new solvent accessible surface that is capable of forming a barrier upon contact with a solvent.

2. The composition of claim 1, wherein the composition, when administered to a mammal, achieves an effective plasma concentration of the active agent from at least about 1 hour to at least about 24 hours after initial administration.

3. The composition of claim 1, wherein at least one of the subunits and the composition from which it was derived have dissolution profiles of the active agent that have a similarity factor of at least 50%.

4. The composition of claim 3, wherein the similarity factor is at least 55%.

5. The composition of claim 1, wherein the composition has a hardness in the range of from about 100 N to about 180 N.

6. The composition of claim 1, wherein the subunits and the intact composition from which they are derived are bioequivalent.

7. The composition of claim 1 comprising from about 20% to about 50% by weight of the active ingredient and from about 20% to about 50% by weight of the starch.

8. The composition of claim 7 comprising from about 35% to about 50% by weight of the active ingredient and from about 20% to about 50% by weight of the starch.

9. The composition of claim 1, wherein the starch is crosslinked with phosphorus oxychloride.

10. The composition of claim 1, wherein the starch comprises hydroxypropyl side chains.

* * * * *